United States Patent [19]

Riazi

[11] Patent Number: 4,632,977

[45] Date of Patent: Dec. 30, 1986

[54] METHOD OF PLASTICIZING THERMOPLASTIC POLYMERS

[75] Inventor: John Riazi, Akron, Ohio

[73] Assignee: The Hygenic Corporation, Akron, Ohio

[21] Appl. No.: 616,053

[22] Filed: Jun. 1, 1984

[51] Int. Cl.$^4$ ............................ C08J 3/18; A61C 5/02
[52] U.S. Cl. ................................... 528/502; 528/950; 523/109; 264/16; 264/40.6; 433/224
[58] Field of Search ................................. 264/40.6, 16; 525/331.9, 333.1; 523/109; 528/502, 950; 241/DIG. 31; 433/224

[56] References Cited

U.S. PATENT DOCUMENTS

| | | | |
|---|---|---|---|
| 2,333,242 | 11/1943 | Fryling | 528/502 |
| 2,693,461 | 11/1954 | Jones | 528/502 |
| 3,414,557 | 12/1968 | Kraus et al. | 528/502 |
| 3,634,381 | 1/1972 | Lehnerer et al. | 528/502 |
| 3,839,250 | 10/1974 | Ehrend et al. | 525/333.1 |
| 4,357,136 | 11/1982 | Herskovitz et al. | 433/224 |

OTHER PUBLICATIONS

Pike et al., J. Polym. Sci., 9(3), pp. 229-251 (1952).
"Rubber Chemistry", Brydson, J. A., Applied Science Publishers Ltd., London, p. 16 (1978).

Primary Examiner—Joseph L. Schofer
Assistant Examiner—F. M. Teskin
Attorney, Agent, or Firm—Renner, Kenner, Greive, Bobak & Taylor

[57] ABSTRACT

A novel process for providing a thermoplastic polymer having novel thermal characteristics including the critical step of masticating the polymer, either continuously or discontinuously, until the melt index of the polymer is substantially increased.

10 Claims, 1 Drawing Figure

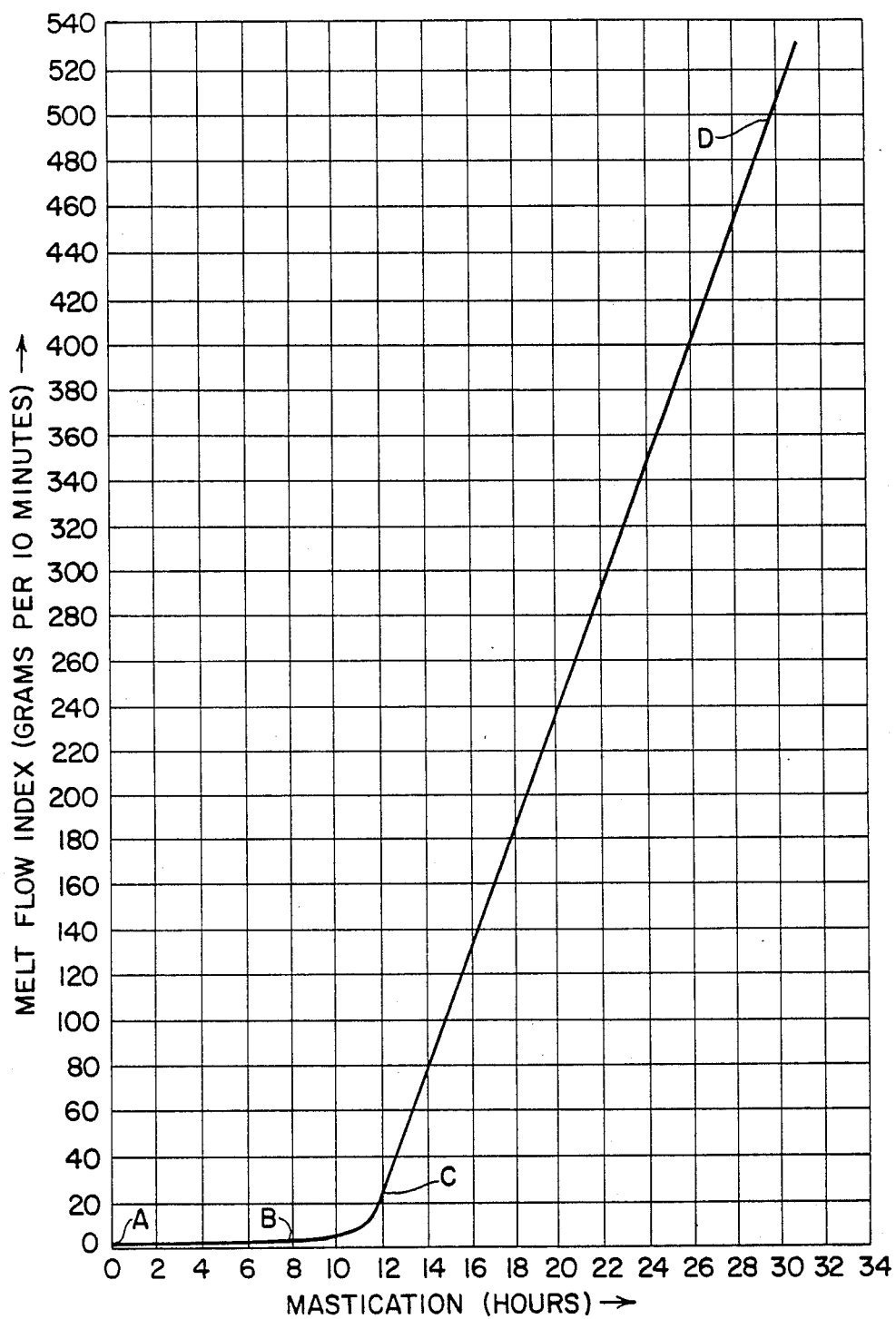

METHOD OF PLASTICIZING THERMOPLASTIC POLYMERS

TECHNICAL FIELD

The present invention relates generally to endodontia methodologies and procedures. More particularly, the present invention relates to the use of thermoplastic polymers in endodontia methodologies and procedures. Specifically, the present invention relates to a method for processing thermoplastic polymers to provide a thermoplastic polymer having a much improved melt flow index so that it is particularly suited for the obturation of root canals.

BACKGROUND ART

Endodontia is a branch of dentistry specializing in diseases of the tooth pulp. A primary corrective procedure for diseased pulp is to remove it, clean out and shape the resulting root canal and then obturate the root canal space. The obturation procedure is critical because if the apical seal is not adequate, the tissues underlying the root canal may be exposed to foreign, deleterious matter.

Obturation of the root canal system typically involves the insertion of a material within the root canal, which material must sealably adhere to the dentin walls. Of particular concern is a fluid-tight seal between the inserted material and the apical foramen region. Additionally, endodontic therapy requires that the inserted material conform, and effect a seal, to the dentin wall irregularities as well as any lateral canals. Various methodologies for obturating root canals have been developed and are disclosed in the prior art. A thorough understanding of these procedures is necessary to appreciate the significance and novelty of the present invention.

While many types of obturating material have been used, modern endodontia techniques utilize trans-polyisoprenes such as gutta-percha and balata or other species thereof. In order to avoid a repetitively detailed identification of the trans-polyisoprenes utilized, the specification will hereinafter simply refer to gutta-percha. Gutta-percha, chemically, is the trans-isomer of natural rubber and is a tough, crystalline, thermoplastic polymer. The thermoplastic characteristic of gutta-percha makes it a particularly useful endodontia material, because in the plasticized state gutta-percha readily adapts to the contour of the dentin walls and tends to retain its shape after cooling, albeit with some shrinkage.

Verification of the effectiveness of a particular obturation technique may be performed in vitro using dye penetrant, radiotracer penetrant, microscopic examination, sectioning, X-ray analysis or scanning electron microscope analysis, among others. Though in vivo assessment is possible, a much greater period of time is required before the results are available. The particular analysis technique utilized will, in part, be determined by which aspect of the obturation seal may be of interest, as well known and understood by those skilled in the art.

One obturation technique involves the use of gutta-percha cones, or points, usually made in standard sizes, a plurality of which are fitted into the root canal which has itself been generally conically shaped to facilitate acceptance of the cones. After the canal has been cleaned and shaped, the dentin walls are typically coated with a sealer and a point is inserted. The inserted point is then condensed with finger pluggers to force the tip of the point into conformation with the apical region of the root canal. With this technique the gutta-percha point typically is not heated, and a second step, lateral condensation, is required. Lateral condensation is effected by inserting additional points into the canal and compacting them with heated finger pluggers to force the point material into lateral conformity with the canal wall, and hopefully to conform the point material not only to the irregularities therein but also to any laterally extending canals. Numerous difficulties can arise with this method. A major inconvenience is having to impart a particular shape to the apex of the canal in order that it can accept a standard gutta-percha point. Irregularities in the dentin walls may allow for a less than satisfactory adaptation of the point to the canal cavity. Also, the sealer may not be uniformly distributed within the interface between the point and the dentin walls.

Another obturation technique is generally referred to as vertical condensation and utilizes heated gutta-percha. The canal is prepared and a sealer introduced, as previously described. The gutta-percha to be introduced into the canal, however, is first heated. A plurality of warmed gutta-percha segments may be compactably inserted into the canal chamber. Heating the gutta-percha reduces its viscosity and thereby allows the material more readily to adapt to the dentin walls than unheated gutta-percha. Unexpectedly, however, the degree of lateral condensation, or conformity, has been found to be reduced.

When employing this technique, it has been found that the material extruded into lateral canals consists primarily of sealer. As anticipated, fillings made by vertical condensation techniques show close adaptation of the gutta-percha to the dentin walls. However, voids are often seen, possibly due to reduced lateral condensation, and the root canal sealer is not always present at the interface. The gutta-percha also tends to cool quickly, particularly during the considerable time required for the vertical condensation technique. Once the material cools, viscosity increases and lateral flow is substantially reduced. Also, seams have been observed which may be indicative of incomplete conjoining of different gutta-percha segments.

A third technique uses a solvent such as chloroform to soften the gutta-percha. While this technique shows good adaptation in the apical region, voids are often seen coronal to this section. The surface of the filling is often wrinkled which is most probably due to shrinkage of the material. Such shrinkage is an undesirable feature as it may reduce the integrity of the required seal between the filling material and the obturated canal. Shrinkage may also occur in the vertical condensation technique during cooling.

The use of plasticizers or other additives in the nature of processing aids has been considered, but there are three major drawbacks. First, it would require lengthy governmental testing and subsequent approval to assure that the processing additives are not deleterious for use in endodontic therapy. Second, even though such approval might be acquired there would be a reluctance on the part of the majority of practitioners to accept a new product without considerable clinical evidence of its satisfactory performance without incident. Third, processing additives appear to create unfavorable shrinkage characteristics which would work to destroy the seal required to obturate a root canal.

Although the above obturation techniques—with perhaps the noted exception as to the use of additives—generally provide reasonably acceptable results when performed properly, but the methods are time consuming and, therefore, costly, and require considerable care to effectuate a fluid-tight seal, particularly at the apical foramen.

One of the most promising obturation techniques is generally referred to as thermoplastic injection of a polymeric material such as gutta-percha. The important feature of this technique is that the polymer is heated to its molten, or plasticized, state—typically about $+160°$ C. The polymer is then forced, under mechanically generated pressure, into the root canal system.

One of the earlier methods for in vitro "thermoplastic injection" is described by Yee, et al, *Three-Dimensional Obturation of the Root Canal Using Injection-Molded, Thermoplasticized Dental Gutta-Percha, JOURNAL OF ENDODONTICS*, Vol. 3, No. 5, May, 1977. The root canal system is shaped and cleaned using conventional techniques. The gutta-percha is next introduced into the root canal cavity using an endodontic pressure syringe. An 18-gauge needle may typically be used inasmuch as it is the maximum size that fits conveniently into the root canal in human anterior teeth.

To prepare for the injection technique, gutta-percha cones are manually loaded into a syringe, and the barrel, with the needle attached, is then heated in a glycerine bath until an unrestrained flow can be achieved. This occurs at about $+160°$ C. The needle is then inserted into the cavity and the gutta-percha extruded therethrough to fill the cavity. When a slight resistance from the injected material is felt, the needle is withdrawn a few millimeters coronally and more material is extruded. This process continues until the canal is completely obturated.

Analysis of the results of obturation by this technique shows few voids and excellent adaptation of the polymer to the dentin walls. A particular advantage is that the plasticized polymer flows both vertically and laterally. Moreover, the sealer tends to be evenly distributed and lateral canals can be effectively obturated.

While the above-described method is useful for in vitro analysis of injection-molded thermoplasticized polymers, clinical application is severely limited due to the excessively high temperatures required to plasticize gutta-percha and similar polymers. These temperatures make handling of the applicator and working in the periapical and oral regions somewhat difficult and possibly unacceptable because of the fear in the mind of the clinician that its use could, even remotely, be injurious to the patient.

In order to circumvent the high temperature related problems which make the injection process clinically undesirable and impractical, much work has been dedicated to developing more feasible delivery systems. One such system is described by Marlin, et al, *Clinical Use of Injection-Molded Thermoplasticized Gutta Percha for Obturation of the Root Canal System: A Preliminary Report, JOURNAL OF ENDODONTICS*, Vol. 7, No. 6, June, 1981. The equipment includes an injection syringe and an electrical heating unit. The barrel of the syringe carries an electrical heating element and is insulated not only to minimize heat dissipation but also to protect the clinician and patient. The level of heat is variable depending, in part, on the needle gauge. Standard gutta-percha points are loaded into the syringe, plasticized, and the gutta-percha is then inserted in a manner similar to the Yee, et al in vitro technique hereinbefore described.

While this method of delivery is an improvement on some aspects of prior known systems, it does necessitate the use of a considerably more complex and expensive delivery system. It must be understood, however, that this method is only a delivery system; it is not a filling system. Tests have revealed that by this procedure the plasticized gutta-percha is delivered only one-half ($\frac{1}{2}$) the distance between the tip of the injection needle and the apex of the canal. Further manipulation, as with finger pluggers, is required to assure that the canal is completely filled. Moreover, the high temperatures at which the gutta-percha must be delivered by this procedure appears, itself, to engender two major drawbacks. First, mental unacceptability—the clinician remains fearful of injecting material at such high temperature into a human patient. Second, questionable operability—it appears that the high temperature differential between the injected gutta-percha and its surrounding environment likely results in excessive shrinkage of the gutta-percha as it cools.

Another method is recounted by Lugassy, et al, *Root Canal Obturation with Gutta-Percha: A Scanning Electron Microscope Comparison of Vertical Compaction and Automated Thermatic Condensation, JOURNAL OF ENDODONTICS*, Vol. 8, Nos. 3, Mar., 1982. The technique was developed by McSpadden and is generally referred to as automated thermatic condensation. This technique uses a compactor, similar to a Hedstroem file, mounted on a contra-angle. The compactor plasticizes the gutta-percha within the root canal system and provides lateral as well as vertical compaction.

According to this technique, after the root canal is shaped and prepared, a compactor size is selected one size smaller than the largest reamer used near the apical constriction. A standard gutta-percha point is inserted into the canal, and the compactor is then rotated at a speed of approximately 10,000–15,000 r.p.m. The direction of rotation must be such as to assure an apical vector for the gutta-percha compaction. Essentially, the rotary tool provides frictional heat whereby the gutta-percha is plasticized and adequate lateral and vertical condensation is achieved.

While the McSpadden technique is an improved method for avoiding the excessive heat problem, the technique still requires sophisticated hardware, consummate skill and strict adherance to specific guidelines to obtain predicted results.

It is clear, therefore, that a viable need exists for an improvement in the art of endodontia whereby thermoplastic polymers can be quickly and inexpensively injected with a minimal risk from excessive temperatures and without elaborate delivery systems.

DISCLOSURE OF THE INVENTION

It is, therefore, a primary object of the present invention to provide an improved process for preparing a material for use in root canal obturation.

It is another object of the invention to provide an obturating material which plasticizes at a clinically feasible temperature and which can be delivered to fill a root canal by virtue of a standard syringe.

It is still another object of the invention to provide a novel improvement to a method of obturating root canals.

It is a further object of the invention to provide a process by which the melt index of a thermoplastic polymer can be substantially increased.

It is yet another object of the present invention to provide an improved process for preparing a thermoplastic material so that the material exhibits minimal shrinkage during cooling.

These and other objects of the invention, as well as the advantages thereof over existing and prior art forms, which will be apparent in view of the following specification, are accomplished by means hereinafter described and claimed.

In general, the present invention relates to a process for plasticization of thermoplastic polymers devoid of plasticizers, solvents or other processing aids as well as a novel thermoplastic polymer having unique characteristics. The polymer is masticated with sufficient shear to heat the polymer. Additionally, heat may be supplied to the polymer, and the mastication is continued for a sufficient period of time that the melt flow index, which is normally about 0.2 grams per ten minutes, will increase to at least about 10 grams per ten minutes. The mastication, if continued for approximately 23 to 32 hours will increase the melt flow index to approximately 500 grams per ten minutes.

The application of the aforesaid process to thermoplastic polymers selected from the group consisting of natural and synthetic trans-polyisoprenes results in a product having novel characteristics and being particularly suited for the obturation of root canals. Typical examples of the trans-species include gutta-percha and balata, although the present invention is not limited to these. As noted hereinabove, reference has been made throughout the specification to gutta-percha as a matter of convenience and because it has been exemplified hereinbelow. Nevertheless, it is to be understood that practice of the present invention is more broadly directed toward the foregoing transpolyisoprenes.

When these materials are processed it has been found that the heat produced by mastication plus the application of additional outside heat sufficient to raise the temperature of the polymer being masticated to approximately the upper reach of the range of approximately 240° to 310° F. (116° to 155° C.). The temperature will slowly decrease during continued mastication, while remaining within the stated range, until such time as the rate of change of the melt flow index undergoes a quantum change. Generally coincident with the quantum change in the rate of change of the melt flow index, as hereinafter more fully explained, the temperature will have reduced approximately twenty to thirty percent (20-30%) from its highest reading. This brings the temperature of the material being masticated down to the range of 190° to 210° F. (88° to 99° C.).

One preferred and one alternative embodiment of a method for producing the novel polymer incorporating the concepts of the present invention are disclosed herein by way of example without attempting to disclose all of the various forms and modifications in which the invention may be carried out; the invention being measured by the appended claims and not by the details of the specification.

BRIEF DESCRIPTION OF THE DRAWING

The drawing FIGURE constitutes a graph in which the most critical quality of the novel polymer—the melt flow index—is plotted against time of mastication.

PREFERRED EMBODIMENT OF THE INVENTION

The plasticization of the thermoplastic polymer according to the concept of the present invention provides a polymer having novel characteristics that are particularly suited for obturating root canals by injection techniques. Specifically, the plasticized polymers so processed will flow sufficiently freely from a needle to fill the full apical cavity and flow laterally to fill any and all irregularities within the canal, and generally even including lateral canals. Moreover, such materials have been found to perfect an effective seal to the dentin walls such that a sealer need not even be employed.

One suitable parameter by which to measure the relative acceptability of a polymer for use as a material by which to fill a root canal is its viscosity. A standardized scale by which to characterize the viscosity of a thermoplastic polymer is its melt flow index.

The melt index is the amount, in grams, of a thermoplastic resin which can be forced through an orifice of 0.0825 inch diameter (2.09 mm) when subjected to a force of 2160 grams in 10 minutes at +105° C. (221° F.). Polymers possessing higher melt flow indices—i.e., on the order of two to three orders of magnitude greater than the normal 0.2 gms/10 min—readily conform to the cavity into which they are injected, and if the melt flow index could be maintained in such an elevated state during the time it takes to perform the filling procedure, the polymer would flow sufficiently to fill the full extent of the canal. Heretofore a sufficiently high melt flow index could be achieved only by elevating the temperatures of the polymer, but unfortunately, the sufficiently higher melt flow index could not be maintained for a period of time to achieve a satisfactory filling of the canal solely by virtue of the flow of the polymer.

According to the concept of the present invention the melt flow index of a thermoplastic polymer such as gutta-percha, balata and the like can be radically and unexpectedly increased by masticating the material for a markedly extended period of time. The masticating operation may be performed with any conventional milling or mixing apparatus, either internal or external, as more fully hereinafter discussed, but the duration of the masticating process is uniquely and substantially modified in a novel way and clearly distinguishable from conventional milling processes.

Milling is one of the well-known processes for masticating, and/or mixing, viscous and elastic materials. A typical two-roll, open mill—as used for mixing, warm-up, feeding and cracking in the rubber industry—may be employed. Such a mill includes two surface rolls, set horizontally close together. The stock material is forced between the rolls, which are rotated at different speeds to form a band of material about at least one of the rolls. The shearing action of the mastication process generates considerable heat. While a typical mixing operation on a mill may require only a few minutes, the processing of a polymer according to the concept of the present invention takes a considerably extended period of time, as hereinafter more fully explained.

Although the preferred embodiment is hereinafter described with particularity in reference to gutta-percha and/or balata, this is to be construed as exemplary only, and not intended to be, in any sense, limiting.

When polymers such as gutta-percha or balata are prepared as the stock material in making "points", cones and the like for endodontic therapy, numerous fillers may be added to the gutta-percha or balata, including barium sulfate, zinc oxide or titanium oxide. The final compound typically is mixed in a conventional milling operation for approximately 20 minutes to an hour.

However, according to the concept of the present invention the polymer is extensively masticated prior to intermixing the fillers normally employed. It should be appreciated that the fillers could well be introduced prior to mastication, but inasmuch as the final product will contain on the order of 19-21 percent gutta-percha, it is more efficient to process the gutta-percha prior to intermixing the standard fillers. Moreover, it has also been found that the process of increasing the melt flow index is facilitated by heating the polymer as it is masticated.

By way of an example, unprocessed gutta-percha has a melt flow index of approximately 0.2 grams per 10 minutes. The normal milling time to intermix the various fillers (20 to 60 minutes) leaves the melt flow index virtually unchanged. In fact, during the first several hours of mastication the melt flow index shows a very modest increase. However, at some point between approximately the 9th and 15th hour there is a totally unexpected quantum increase to the rate of change of the melt flow index per hour of mastication such that continued mastication for an additional, comparable period of time effects change in the melt flow index on the order of at least two orders of magnitude.

The masticating itself creates some heat, and this heat is augmented by passing steam through, for example, the mill rolls employed in the masticating procedure. If the steam is under approximately one atmosphere pressure, that heat plus the heat supplied by the shearing of the polymer during masticating will cause the temperature of the polymer being masticated to rise initially to a range of from about 295° to 310° F. (146° to 154° C.). This appears to be an effective temperature for the initial mastication of gutta-percha on a steam heated, open mill. Those skilled in the art will appreciate that in a closed, internal mixer, for example, or any mixer in which pressurized steam or other high temperature heating means—e.g., hot oil—might effect attaining the higher melt flow index in a shorter time.

When the melt flow index has been markedly increased, the temperature induced by the shear of mastication is greatly reduced. In fact, the temperature of the gutta-percha has been found to display an overall decrease on the order of 20% to 30% at or shortly after the aforedescribed quantum increase in the rate of change of the melt flow index—even as the mastication process is continued. Specifically, the temperature of the gutta-percha is reduced to the range of from about 190° to 210° F. (88° to 99° C.).

In order to quantify this wholly unexpected result a 2500 gram batch of unprocessed gutta-percha was continuously masticated in an open mill for 27 hours. Steam under approximately one atmosphere of pressure was supplied to the mill rolls. The temperature of the gutta-percha was noted every 30 minutes, and a sample of the gutta-percha was taken every hour and tested by the standard procedure described above to determine the melt flow index. Those results are set forth below in Table I.

TABLE I

Melt Flow Index and Temperature Determined at Stated Intervals During Mastication

| Time (Hours) | Temperature °F. (°C.) | Melt Flow Index (Gms/10 min) |
|---|---|---|
| 0 | 310° (154°) | 0.225 |
| 0.5 | 310° (154°) | |
| 1.0 | 312° (156°) | 0.233 |
| 1.5 | 305° (152°) | |
| 2.0 | 300° (149°) | 0.361 |
| 2.5 | 295° (146°) | |
| 3.0 | 295° (146°) | 0.435 |
| 3.5 | 290° (143°) | |
| 4.0 | 295° (146°) | 0.539 |
| 4.5 | 297° (147°) | |
| 5.0 | 290° (143°) | 0.611 |
| 5.5 | 283° (139°) | |
| 6.0 | 280° (138°) | 0.70 |
| 6.5 | 275° (135°) | |
| 7.0 | 275° (135°) | 0.79 |
| 7.5 | 278° (137°) | |
| 8.0 | 278° (137°) | 0.95 |
| 8.5 | 278° (137°) | |
| 9.0 | 270° (132°) | 1.14 |
| 9.5 | 270° (132°) | |
| 10.0 | 270° (132°) | 1.25 |
| 10.5 | 268° (131°) | |
| 11.0 | 271° (133°) | 1.50 |
| 11.5 | 268° (131°) | |
| 12.0 | 270° (132°) | 2.33 |
| 12.5 | 260° (127°) | |
| 13.0 | 260° (127°) | 4.9 |
| 13.5 | 260° (127°) | |
| 14.0 | 230° (110°) | 11.64 |
| 14.5 | 230° (110°) | |
| 15.0 | 230° (110°) | 46.7 |
| 15.5 | 205° (96°) | |
| 16.0 | 205° (96°) | 88.0 |
| 16.5 | 200° (93°) | |
| 17.0 | 200° (93°) | 129.2 |
| 17.5 | 200° (93°) | |
| 18.0 | 210° (99°) | 168.8 |
| 18.5 | 210° (99°) | |
| 19.0 | 205° (96°) | 214.9 |
| 19.5 | 210° (99°) | |
| 20.0 | 210° (99°) | 245.5 |
| 20.5 | 205° (96°) | |
| 21.0 | 205° (96°) | 276.2 |
| 21.5 | 200° (93°) | |
| 22.0 | 203° (95°) | 275 |
| 22.5 | 220° (104°) | |
| 23.0 | 225° (107°) | 314 |
| 23.5 | 220° (104°) | |
| 24.0 | 225° (107°) | 373 |
| 24.5 | 220° (104°) | |
| 25.0 | 225° (107°) | 384 |
| 25.5 | 220° (104°) | |
| 26.0 | 220° (104°) | 424 |
| 26.5 | 210° (99°) | |
| 27.0 | 200° (93°) | 480 |

The change in the melt flow index observed during the first several hours would provide no motivation to continue the mastication precedure. What is, therefore, unexpected is that by continuing for what might have been deemed an inordinate period of time one can perceive an increase in the melt flow index from the approximate 0.2 gms/10 minute for unprocessed gutta-percha up to approximately 500 gms/10 minutes—a 2500 fold increase.

In the examples which follow seven samples of gutta-percha ranging between 1700 to 2500 grams each, were separately masticated on a two-roll mill. The mill temperature of the stock was initially raised to approximately 310° F. (154° C.) with steam. Milling continued for various periods of times ranging from about 23 hours to 32 hours. Melt flow indices were determined for each example and have been reported in Table II hereinbelow along with the total milling time.

TABLE II

Melt Flow Index After Continued Mastication

| Example No. | Total Mastication Time (Hours) | Melt Flow Index (gms/10 min) |
|---|---|---|
| 1 | 23 | 511 |
| 2 | 29.75 | 479 |
| 3 | 24 | 494 |
| 4 | 24 | 521.7 |
| 5 | 27.25 | 495.9 |
| 6 | 32 | 541.9 |
| 7 | 27 | 480 |

The foregoing examples were processed by adding the externally applied heat, as described above, and it would be expected that whereas one might ultimately be able to achieve the desired melt flow index without adding external heat, it would also be anticipated that the mastication time would likely be extended to 10 to 14 days to achieve the desired melt flow index, just as the aforestated higher temperature might reduce the time to less than 24 hours.

Thereafter, the customary additives, such as those identified above, can be intermixed into the gutta-percha by a 20 to 60 minute milling process. The additives will tend to reduce the melt flow index on the order of at least 50%. This decrease was obviated by additional milling for about 3.25 hours. Approximately 1.5 hours of cold milling followed by 1.75 hours of milling with steam, restored the melt index to 500 grams per 10 mintues. Those skilled in the art will readily appreciate that various combinations of increased milling can be employed. Gutta-percha having such a markedly increased melt flow index may be heated to approximately 158° F. (70° C.) and injected through a needle fully to fill the entire cavity of a root canal. The gutta-percha so processed flows the full distance from the needle to the apex of the canal. Moreover, gutta-percha so processed will flow fully to the apex and laterally into any and all irregularities, usually including lateral canals, all without requiring additional manipulation with finger pluggers or the like.

Gutta-percha with such an increased melt flow index also appears more effectively to "wet" the dentin wall and seal the same without the necessity of employing a separate sealer. Finally, the gutta-percha so processed does not as readily pull away from the walls as a result of shrinkage as it cools, thus maintaining the necessary seal.

According to the concepts of the present invention, the melt flow index, as previously defined, of the polymer may be substantially changed by performing either the heretofore described continuous masticating operation or, alternatively, an intermittent masticating operation.

Intermittent mastication involves mastication for a stated period of time and then allowing the material to rest and cool for a sufficient period of time to permit it to recrystallize. This cycle may be repeated until the desired melt flow index is achieved. Although this procedure appears initially to increase the melt flow index with somewhat less actual mastication time, the start/stop procedure tends to make the procedure somewhat inconvenient for commercial application.

Moreover, it is believed that any reduction in the actual mastication time is effected only during that period prior to the quantum increase in the rate of change of the melt flow index in response to mastication. That is, prior to the knee of the curve set forth in the FIGURE.

The FIGURE is a plot of the melt flow index versus time, comparable to the relationship set forth in Table I. Each axis is a linear scale, the abscissa being the time axis, in hours, and the ordinate being the melt flow index axis, in grams/10 minutes.

Nine separate batches were run with samplings taken and tested, all in the same manner as described in conjunction with Table I. The results were plotted on a graph having axes conforming to those identified in the FIGURE, and by the method of least squares regression analysis those runs were reduced to the single representative plot depicted in the FIGURE. Mastication for approximately that period of time represented between points A and B on the curve depicted in the FIGURE revealed the existence of a generally linear relationship between the melt flow index and the time of mastication. That relationship can be expressed generally by the linear equation $y = 0.2414x - 0.0883$.

Between points B and C there is a pronounced change in the slope of the curve. This is the "knee" of the curve, and it represents a transitional range heretofore designated as the quantum change. This knee was found to occur within a total range of between 8 to 16 hours, with the majority of the samplings reflecting the occurrence of the knee with an approximate range of from 9 to 13 hours. It was also noted that the knee was fairly well developed by the time the melt flow index reached approximately 10 grams/10 minutes, irrespective of the mastication time required to bring the melt flow index to that level.

From point C to, and past, point D the plot was a totally different slope than encountered between points A and B. A generally linear relationship was also determined to exist between the melt flow index and the time of mastication beyond the "knee." This relationship can be expressed generally by the linear equation $y = 26.5227x - 294.0156$.

Mathematically, the curve $y = f(x)$ graphically represents any function "y" of a single variable "x". The graph of a linear function is represented by $y = mx + b$, where "m" is the slope of the "curve" (a line) and "b" equals the "y" intercept. Thus, the slope of the linear relationship between points A and B equals approximately 0.2414, and the slope of the linear relationship between points C and D equals approximately 26.5227. This is a change in excess of two orders of magnitude.

Within the time frame from points A to B, there is no indication that continued mastication would produce the transitional rate of change represented by the knee nor that the plot would thereafter slope more favorably to reflect markedly higher and higher melt flow indices with respect to relatively modest further mastication time.

The significance of this novel process is critical in fields such as endodontia. By increasing the melt index of the polymer, thermoplastic injection molding can be performed at much lower and safer temperatures, such as about +150° F. (66° C.). Such lower plasticization temperatures make clinical application of this technique readily available and obviate the need for sophisticated delivery systems or alternative obturation techniques. By processing the gutta-percha in accord with the novel process disclosed herein, the polymer can be plasticized at a clinically more acceptable temperature. The lower temperature also minimizes shrinkage of the material upon cooling, thus improving the integrity of the seal. It will also be appreciated by one skilled in the art that use of a higher melt-index polymer with other obturation techniques such as, for example, lateral and vertical condensation and automated thermatic condensation, will greatly enhance the utility of those techniques.

The exact milling criteria will, of course, be dependent on the particular flow characteristic desired for the material and the particular use to be made thereof. Inasmuch as the present invention is subject to many variations and changes in detail, a number of which have been expressly stated herein, it is intended that all matter described throughout this entire specification be interpreted as illustrative rather than limiting.

It must be appreciated that for the endodontic procedures presently contemplated a melt flow index of 500 grams per 10 minutes has been found to be perfectly adequate. As a result, no attempts have been made to continue mastication beyond that point. It should also be understood that there have been no indications that would dissuade one from believing that even higher melt flow indices could be obtained by appropriately increased mastication times.

It should thus be evident that a material prepared according to the concepts of the present invention, or reasonably equivalent methods, will accomplish the objects of the present invention and otherwise substantially improve the art of thermoplastic polymers.

I claim:

1. A process for the plasticization of thermoplastic polymers selected from the group consisting of gutta-percha, balata and synthetic transpolyisoprene having an unprocessed melt flow index falling within the range of approximately 0.2 to 0.8 grams per 10 minutes and being devoid of plasticizers, solvents or other chemical processing aids comprising the steps of:
   masticating said polymer with sufficient shear to heat the polymer;
   applying additional heat to said polymer as it is masticated in an amount sufficient to raise the temperature of said polymer to about 295°0 F.; and,
   discontinuing the mastication of said polymer when the melt index reaches approximately a 500 gram flow per 10 minutes.

2. A process, as set forth in claim 1, wherein said thermoplastic polymer is selected from the group consisting of gutta-percha and balata.

3. A process for the plasticization of thermoplastic polymers selected from the group consisting of gutta-percha, balata and synthetic transpolyisoprene having an unprocessed melt flow index falling within the range of approximately 0.2 to 0.8 grams per 10 minutes and being devoid of plasticizers, solvents or other chemical processing aids comprising the steps of:
   masticating said polymer with sufficient shear to heat the polymer;
   applying additional heat to said polymer as it is masticated in an amount sufficient to raise the temperature of said polymer to a range of from about 295° to 310° F.;
   monitoring the temperature of said polymer as it is masticated; and,
   discontinuing said masticating step when the temperature of said polymer drops to a range of from about 190° to 210° F.

4. A process for the plasticization of a thermoplastic polymer wherein said thermoplastic polymer is selected form the group consisting of gutta-percha, balata, and synthetic trans-polyisoprene having an unprocessed melt flow index falling within the range of approximately 0.2 to 0.8 grams per 10 minutes and being devoid of plasticizers, solvents or other chemical processing aids, said process comprising the steps of:
   masticating the polymer with sufficient shear to create heat;
   continuing the mastication for a period of approximately 23 to 32 hours; wherein said heat is created in an amount sufficient to raise the temperature of said polymer initially to a range of from about 295° to 310° F.; and
   wherein said step of mastication is continued until at least the temperature of said polymer drops to a range of from about 190° to 210° F.; and,
   thereafter discontinuing the mastication.

5. A process, as set forth in claim 4, wherein the mastication is continued until the melt flow index is at least 100 grams per 10 minutes.

6. A process, as set forth in claim 4, wherein the mastication is continued until the melt flow index is up to approximately 500 grams per 10 minutes.

7. A process for the plasticization of thermoplastic polymers selected from the group consisting of gutta-percha, balata and synthetic trans-polyisoprene having an unprocessed melt flow index falling within the range of approximately 0.2 to 0.8 grams per 10 minutes and being devoid of plasticizers, solvents or other chemical processing aids comprising the steps of:
   masticating the polymer;
   noting the relationship of the polymer melt flow index to the time of mastication which is linear and defines a positive slope;
   continuing said mastication until at least the transitional range is achieved, where an increase of at least an order of magnitude in the value of the positive slope occurs.

8. A process, as set forth in claim 7, wherein the mastication is continued until the melt flow index is at least 100 grams per 10 minutes.

9. A process, as set forth in claim 7, wherein mastication is continued until the melt flow index reaches up to approximately 500 grams per 10 minutes.

10. A process, as set forth in claim 7, wherein the function of the melt flow index in relation to the time of mastication both before and after the transitional range can be expressed in terms of the linear equation $y = mx + b$ and wherein m after the transitional range is approximately two orders of magnitude greater than prior to the transitional range.

* * * * *

UNITED STATES PATENT AND TRADEMARK OFFICE
CERTIFICATE OF CORRECTION

PATENT NO. : 4,632,977

DATED : December 30, 1986

INVENTOR(S) : John Riazi

It is certified that error appears in the above-identified patent and that said Letters Patent is hereby corrected as shown below:

Column 11, claim 1, line 42, "295°O F" should read -- 295°F --.

Column 12, claim 4, line 10, "form" should read -- from --.

Signed and Sealed this

Tenth Day of November, 1992

Attest:

DOUGLAS B. COMER

Attesting Officer

Acting Commissioner of Patents and Trademarks